United States Patent
Tsai et al.

(10) Patent No.: US 8,790,738 B2
(45) Date of Patent: Jul. 29, 2014

(54) PROCESS OF PREPARING BURDOCK COMPOSITE MICRON ESSENCE

(75) Inventors: Tong-Rong Tsai, Kaohsiung (TW); Hsueh-Chiao Liu, Pingtung County (TW)

(73) Assignee: Dong Yuan Biotech Pharmaceutical Co., Ltd, Kaohsiung (TW)

( * ) Notice: Subject to any disclaimer, the term of this patent is extended or adjusted under 35 U.S.C. 154(b) by 139 days.

(21) Appl. No.: 13/555,392

(22) Filed: Jul. 23, 2012

(65) Prior Publication Data
US 2013/0084380 A1      Apr. 4, 2013

(30) Foreign Application Priority Data
Sep. 29, 2011   (TW) .............................. 100135370 A

(51) Int. Cl.
*A23L 1/30*   (2006.01)
*A61K 36/28*   (2006.01)
*A23L 1/035*   (2006.01)

(52) U.S. Cl.
CPC .............. *A61K 36/28* (2013.01); *A23L 1/035* (2013.01); *A23L 1/3002* (2013.01)
USPC ........................................... 426/648; 426/655

(58) Field of Classification Search
CPC ........................................................ A23L 1/30
USPC ........................................................ 426/648
See application file for complete search history.

(56) References Cited

U.S. PATENT DOCUMENTS 3,424,592 A  *  1/1969  Heinz ........................... 426/602
2008/0175930 A1 *  7/2008  Baseeth ......................... 424/742

* cited by examiner

*Primary Examiner* — Patricia George
(74) *Attorney, Agent, or Firm* — Jackson IPG PLLC

(57) ABSTRACT

A process of preparing a burdock composite micron essence at least includes the following. Dissolved and heated phospholipid is added to a vegetable oil extract and then stirred. After stirring, the above mixture is pour into a heated glycerol and then further stirred and a burdock extract aqueous solution is added. The aforementioned mixed solution is stirred at high speed, the emulsion-homogenized solution is subject to high-pressure homogenization, and a filtration membrane is used to filter the homogenized solution obtained to get a purple transparent burdock concentrate. The burdock concentrate is used to prepare the formulation of nano-micro emulsion which is easily absorbed by human body and thus grants improved health benefits.

9 Claims, 1 Drawing Sheet

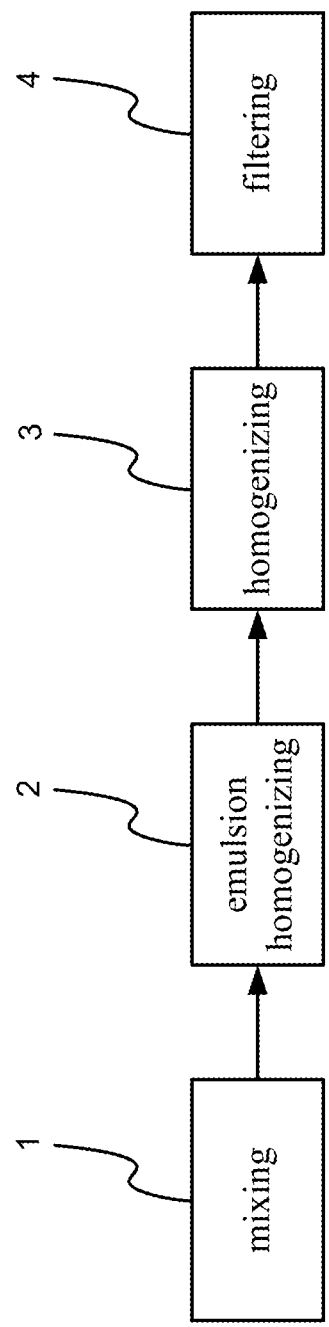

PROCESS OF PREPARING BURDOCK COMPOSITE MICRON ESSENCE

BACKGROUND OF THE INVENTION

1. Field of the Invention

The present invention relates to a process of preparing a burdock composite micron essence, and particularly to a process of preparing a burdock composite micron essence, in which a burdock concentrate is used to prepare the formulation of nano-micro emulsion which is easily absorbed by human body and thus grants improved health benefits.

2. Description of Related Art

Burdock (*Arctium lappa* Linn,) belongs to the Asteraceae herbs, with English alias being the great burdock, and is a kind of health food of high nutritional value. It is very rich in nutrients, including inulin, polyphenols, chlorogenic acid, proteins, carbohydrates, vitamins, amino acids, minerals and unsaturated fatty acids. Additionally, its carotene content is higher than carrots by 150 times. It has high amino acid content as well. Burdock has been applied to the health food in Chinese-speaking regions for long time for its high nutritional value.

However, a burdock composite essence in the prior art is prepared in form of nanomicell solution. The nanomicell solution contains an oil phase, an emulsifier and a small amount of aqueous phase. After oral administration, the nanomicell solution will be uniformly and rapid dispersed into a nano-micro emulsion of about 100 nm to cover the gastric mucosa as soon as meets water. Effective ingredients in such a formulation are Shikonin and *Angelica*, which are more soluble in oil phase, will suffer a poor health effect after oral administration for the oil phase being not soluble in water.

SUMMARY OF THE INVENTION

This invention aims at providing a method of preparing a burdock composite micron essence, in which a burdock concentrate is used to prepare the formulation of nano-micro emulsion which is easily absorbed by human body and thus grants improved health benefits.

In order to achieve the above and other objectives of the invention, the method of preparing a burdock composite micron essence at least includes: Step of mixing: dissolved and heated phospholipid is added to a vegetable oil extract and then stirred; after stirring, the above mixture is pour into a heated glycerol and then further stirred; and a burdock extract aqueous solution is added; Step of emulsion homogenizing: the aforementioned mixed solution is stirred at high speed; Step of homogenizing: the emulsion-homogenized solution is subject to high-pressure homogenization; and Step of filtering: a filtration membrane is used to filter the homogenized solution to get a purple transparent burdock concentrate.

In one embodiment of the invention, at Step of mixing, the phospholipid is dissolved in alcohol, heated in water bath, and ready for use after the alcohol is evaporated.

In one embodiment of the invention, at Step of mixing, the vegetable oil extract is at lease on selected from sesame oil extract, *angelica* extract and *lithospermum* extract, or mixture thereof, and is ready for use after being heated in water bath at 80° C.

In one embodiment of the invention, at Step of mixing, the glycerol is ready for use after heated in water bath at 80° C.

In one embodiment of the invention, at Step of emulsion homogenizing, the mixed solution is stirred at high speed in a high-speed emulsion homogenizer.

In one embodiment of the invention, at Step of emulsion homogenizing, the time for high-speed stirring is 2-4 min.

In one embodiment of the invention, at Step of homogenizing, the emulsion-homogenized solution is subject to high-pressure homogenization by a high-pressure homogenizer for five cycles (8000 psi).

In one embodiment of the invention, at Step of filtering, the filtration membrane is a 0.1 µm filtration membrane.

In one embodiment of the invention, the burdock concentrate includes 15% of oil, 5% of lecithin, 60% of glycerol and 20% of burdock extract.

BRIEF DESCRIPTION OF THE DRAWINGS

FIG. 1 is a block diagram of a process of preparing a burdock composite micron essence according to one embodiment of the invention.

DETAILED DESCRIPTION OF THE PREFERRED EMBODIMENTS

The aforementioned illustrations and following detailed descriptions are exemplary for the purpose of further explaining the scope of the present invention. Other objectives and advantages related to the present invention will be illustrated in the subsequent descriptions and appended tables.

Please refer to FIG. 1 which is a block diagram of a process of preparing a burdock composite micron essence according to one embodiment of the invention. As shown, the process of preparing a burdock composite micron essence at least includes Step 1 of mixing, Step 2 of emulsion homogenizing, Step 3 of homogenizing and Step 4 of filtering as follows:

Step 1 of mixing: Phospholipid is dissolved in alcohol, heated in water bath, and ready for use after the alcohol is evaporated. The above phospholipid is added to a vegetable oil extract and then stirred. After stirring, the above mixture is pour into a heated glycerol and then stirred further for a predetermined period of time. Then, the burdock extract aqueous solution is added. The oil extract can be at lease on selected from sesame oil extract, *angelica* extract and *lithospermum* extract, or mixture thereof, and is ready for use after being heated in water bath at 80° C. The glycerol is ready for use after heated in water bath at 80° C.

Step 2 of emulsion homogenizing: The aforementioned mixed solution is stirred at high speed in a high-speed emulsion homogenizer. The time for high-speed stirring is 2-4 min.

Step 3 of homogenizing: The emulsion-homogenized solution is subject to high-pressure homogenization by a high-pressure homogenizer for five cycles (8000 psi).

Step 4 of filtering: Finally, a 0.1 µm filtration membrane is used to filter the homogenized solution obtained at Step 3 to get a purple transparent burdock concentrate containing 15% of oil, 5% of lecithin, 60% of glycerol and 20% of burdock extract.

The obtained burdock concentrate can be used to prepare the formation of nano-micro emulsion. It is easily absorbed by human body after oral administration, granting improved health benefit. Therefore, a new process of preparing a burdock composite micron essence is achieved in the above way.

In summary, the process of preparing the burdock composite micron essence according to the invention effectively improves the shortcomings of the prior art, and uses the burdock concentrate to prepare the formulation of nano-micro emulsion which is easily absorbed by human body and thus grants improved health benefits.

The descriptions illustrated supra set forth simply the preferred embodiments of the present invention; however, the characteristics of the present invention are by no means restricted thereto. All changes, alternations, or modifications conveniently considered by those skilled in the art are deemed to be encompassed within the scope of the present invention delineated by the following claims.

What is claimed is:

1. A process of preparing a burdock composite micron essence, comprising
    Step 1 of mixing: phospholipid is dissolved and heated and then added to a vegetable oil blend and then stirred to obtain a mixture; after stirring, the mixture is poured into heated glycerol and further stirred; and a burdock extract aqueous solution is added to obtain a mixed solution;
    Step 2 of emulsion homogenizing: the mixed solution from Step 1 is stirred at high speed to obtain an emulsion-homogenized solution;
    Step 3 of homogenizing: the emulsion-homogenized solution is subject to high-pressure homogenization to obtain a homogenized solution; and
    Step 4 of filtering: a filtration membrane is used to filter the homogenized solution obtained at Step 3 to get a purple transparent burdock concentrate wherein the filtration produces a micron essence.

2. The process of preparing a burdock composite micron essence of claim 1, wherein the phospholipid is dissolved and heated by dissolving the phospholipid in alcohol, and heating the phospholipid alcohol in a water bath to evaporate the alcohol before adding the phospholipid to the vegetable oil blend.

3. The process of preparing a burdock composite micron essence of claim 1, wherein the vegetable oil blend is a mixture of sesame oil, *angelica* extract, and lithospermum extract, and wherein the vegetable oil blend is added to the phospholipid after the vegetable oil blend is heated in a water bath to 80 ° C.

4. The process of preparing a burdock composite micron essence of claim 1, wherein the heated glycerol is heated in a water bath to 80 ° C.

5. The process of preparing a burdock composite micron essence of claim 1, wherein in Step 2, the mixed solution is stirred at high speed in a high-speed emulsion homogenizer.

6. The process of preparing a burdock composite micron essence of claim 1, wherein in Step 2, the high-speed stirring is for 2-4 min.

7. The process of preparing a burdock composite micron essence of claim 1, wherein in Step 3, the emulsion-homogenized solution is subject to high-pressure homogenization by a high-pressure homogenizer for five cycles (8000 psi).

8. The process of preparing a burdock composite micron essence of claim 1, wherein at the Step of filtering, the filtration membrane is a 0.1 µm filtration membrane.

9. The process of preparing a burdock composite micron essence of claim 1, wherein the phospholipid is lecithin and the burdock composite micron essence consists of 15% of vegetable oil blend, 5% of lecithin, 60% of glycerol and 20% of burdock extract aqueous solution.

* * * * *